United States Patent [19]

Madrange et al.

[11] Patent Number: 5,344,464
[45] Date of Patent: * Sep. 6, 1994

[54] OXIDATION DYE COMPOSITION CONTAINING AT LEAST ONE DOUBLE BASE IN COMBINATION WITH AT LEAST ONE SINGLE BASE AND DYEING PROCESS MAKING USE OF IT

[75] Inventors: Annie Madrange, Saint-Germain-en-Laye; Jean Marie Millequant, Saint-Maur, both of France

[73] Assignee: L'Oreal, Paris, France

[*] Notice: The portion of the term of this patent subsequent to Aug. 11, 2009 has been disclaimed.

[21] Appl. No.: 903,131

[22] Filed: Jun. 23, 1992

Related U.S. Application Data

[63] Continuation of Ser. No. 747,500, Aug. 19, 1991, Pat. No. 5,137,538, which is a continuation of Ser. No. 404,427, Sep. 8, 1989, abandoned.

[30] Foreign Application Priority Data

Sep. 8, 1988 [FR] France ................................ 88 11739

[51] Int. Cl.⁵ ................................................ A01K 7/13
[52] U.S. Cl. ............................................ 8/410; 8/407; 8/408; 8/411; 8/412; 8/416; 8/421
[58] Field of Search .................... 8/407, 408, 410, 411, 8/412, 416, 421

[56] References Cited

U.S. PATENT DOCUMENTS

| | | | |
|---|---|---|---|
| 4,268,264 | 5/1981 | Grollier et al. | 8/410 |
| 4,370,142 | 1/1983 | Bugaut et al. | 8/421 |
| 4,842,612 | 6/1989 | Rose et al. | 8/411 |
| 5,114,429 | 5/1992 | Junino et al. | 8/410 |
| 5,137,538 | 8/1992 | Madrange et al. | 8/410 |
| 5,180,399 | 1/1993 | Grollier et al. | 8/405 |

FOREIGN PATENT DOCUMENTS

| | | |
|---|---|---|
| 2934329 | 2/1988 | Fed. Rep. of Germany . |
| 2016123 | 5/1970 | France . |
| 2018302 | 10/1979 | United Kingdom . |
| 2018836 | 10/1979 | United Kingdom . |
| 2205329 | 12/1988 | United Kingdom . |

OTHER PUBLICATIONS

Billmeyer & Saltzman, Principles of Color Technology, published by John Wiley & Sons, 1966, pp. 25–29.
Nickerson et al., Journal of the Optical Society of America, vol. 34, No. 9, Sep. 1944, pp. 550–570.

Primary Examiner—Linda Skaling
Attorney, Agent, or Firm—Jacobson, Price, Holman & Stern

[57] ABSTRACT

The invention relates to dye compositions for keratinous fibres, containing:
(a) at least one dye precursor belonging to group (A) of single bases chosen from para-phenylenediamines;
(b) at least one dye precursor of group (B) of double bases chosen from N,N'-diphenylalkylenediamines;
the dye precursors of groups (A) and (B) being chosen so that the intensity of the colour on dyed bleached hair ($V_B$) and the intensity on dyed permanent-waved bleached hair ($V_{PB}$) is such that $V_B - V_{PB} = 0 \pm 0.5$, the values of intensity or "value" being determined according to the Munsell notation, the molar ratio of the single bases of group (A) to the double bases of group (B) being between 3 and 10.

24 Claims, No Drawings

OXIDATION DYE COMPOSITION CONTAINING AT LEAST ONE DOUBLE BASE IN COMBINATION WITH AT LEAST ONE SINGLE BASE AND DYEING PROCESS MAKING USE OF IT

This is a continuation of application Ser. No. 747,500, filed Aug. 19, 1991, now U.S. Pat. No. 5,137,538 which is a continuation of Ser. No. 404,427, filed Sep. 8, 1989, now abandoned.

The present invention relates to compositions intended to be employed in dyeing keratinous fibres, particularly human keratinous fibres, and especially human hair, containing so-called "double" oxidation bases and so-called "single" oxidation bases and to the dyeing processes making use of such compositions.

It is known to employ, for dyeing keratinous fibres, particularly human hair, dye compositions containing oxidation dyes such as compounds which are also called "oxidation bases or oxidation dye precursors".

These oxidation bases are not dyes in themselves, but are capable of developing their dyeing power in an oxidizing medium to give dyes by a process of oxidative condensation either of the oxidation dye precursor with itself or of the base or oxidation dye precursor with a compound called "tinter or coupler".

These oxidation dye precursors can be employed by themselves or in combination with other dyes, especially "direct" dyes such as the nitro dyes of the benzene series, anthraquinones and azo compounds.

It cannot be denied that "oxidation" bases and more particularly para-phenylenediamines offer advantages. They have a good affinity for keratinous fibres on which, in general, they make it possible to produce a wide variety of colours which stand up satisfactorily to light radiation and to repeated washing.

However, while acceptable colouring results and tenacities are obtained on most heads of hair with the oxidation dye precursors belonging to the para-phenylene-diamine group, a rejection of the colour and poor tenacity are found when these dye compositions are applied to hair which has repeatedly been subjected to sensitizing hair treatment such as bleaching or permanent-waving or else bleaching and permanent-waving.

Thus, on hair which is partly highly sensitized, major differences in shades between the part close to the root and the highly sensitized end are obtained already on the day of the dyeing. Because of the poor behaviour on the damaged part it is also found that this difference increases progressively with time instead of diminishing with the passage of days and with shampooing.

To overcome this problem, a first solution proposed previously in the state of the art consisted in introducing into the dye compositions cationic macromolecules which, by reducing the sensitization, permit a better uniformity and result in shades which do indeed stand up better to washing.

A second solution was the introduction into the dye compositions of bases and/or couplers of a high molecular weight, obtained with the aid of oxidation dye precursors bearing various substitutions on the nitrogen atoms or directly on the benzene nucleus. This solution makes it possible to produce more uniform and more tenacious shades when a part of the head of hair is moderately sensitized and especially when dark shades which range from the brown to black are considered.

The Applicant has found, however, that even in the case of formulations improved in this way, the performance still remains relatively unimpressive when the ends of the hair are highly sensitized and when it is desired to obtain uniform and tenacious shades ranging from brown to light blond over the whole head of hair. A lack of uniformity is found, in fact, due to the rejection of the colour and poor behaviour on repeated washing.

The Applicant has found, and this forms the subject of the invention, that it was possible to obtain major increases in uniformity and in behaviour on repeated washing by combining with "single" oxidation bases of the para-phenylenediamine group, in accordance with rules which will be defined hereinafter, more complex oxidation bases of the N,N'-diphenylalkylenediamine group, also called "double bases".

Most of these bases are known per se and are described in particular, in French Patent 2 016 123 or in U.S. Pat. No. 3,694,138.

The Applicant has further found, surprisingly, that it was possible to obtain a colour exhibiting good uniformity and retaining this property, even after repeated washing, over the whole length of the hair, even when highly sensitized over part of it.

The subject of the invention is consequently dye compositions for keratinous fibres and in particular for human hair, comprising the combination defined above.

Another subject of the invention consists of the process for dyeing keratinous fibres, in particular human hair, making use of such a combination.

Other subjects of the invention will become apparent on reading the description and the examples which follow.

The dye composition in accordance with the invention is essentially characterized in that it comprises, in a suitable medium for dyeing keratinous fibres:

(a) at least one dye precursor belonging to the group (A) of single bases chosen from para-phenylene-diamines of formula:

in which $R_1$, $R_2$, $R_3$ and $R_4$, independently of one another, denote a hydrogen or halogen atom or an alkyl or alkoxy radical, as well as the salts of these compounds;

(b) at least one dye precursor from the group (B) of double bases chosen from N,N'-diphenylalkylenediamines, corresponding to the formula:

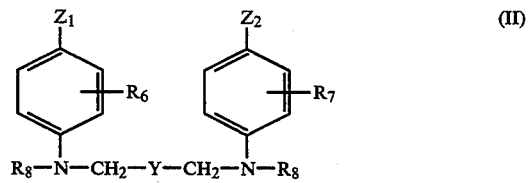

in which:

$Z_1$ and $Z_2$, which are identical or different, denote hydroxyl or $NHR_9$ groups, in which $R_9$ denotes a hydrogen atom or an alkyl radical;

$R_6$ and $R_7$, which are identical or different, denote either hydrogen atoms or halogen atoms or else alkyl groups; $R_8$ denotes a hydrogen atom or an alkyl, hydroxyalkyl or aminoalkyl group; the amino residue may be substituted by an alkyl group;

Y denotes a radical taken from the group consisting of the following radicals:

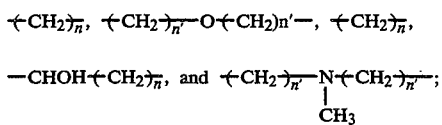

n being an integer between 0 and 8 and n' being an integer between 0 and 4, as well as their addition salts with acids.

The salts are chosen from cosmetically acceptable salts such as hydrochlorides, hydrobromides, sulphates and similar salts.

In formulae (I) and (II) the alkyl and alkoxy groups preferably contain from 1 to 4 carbon atoms, the hydroxyalkyl group preferably has from 2 to 4 carbon atoms and the aminoalkyl group preferably has from 1 to 4 carbon atoms.

The dyes of the (A) and (B) groups are chosen so that the intensity of the colour on dyed bleached hair ($V_B$) and the intensity on dyed permanent-waved bleached hair ($V_{PB}$) is such that $V_B - V_{PB} = 0 \pm 0.5$, the values of intensity or "value" being determined according to the Munsell notation.

Insofar as the Munsell notation is concerned, reference may be made to ASTM standards D1535-68. According to this notation, a colour is defined by the formula HV/C, in which the three parameters refer respectively to the shade (or hue) (H), the intensity (or Value) (V) and the purity (or chromaticity) (C), the oblique stroke being a mere convention.

In accordance with the invention and to determine the condition linking the intensities, "bleached hair" is the term applied to hair which has been treated for approximately 45 minutes with an oxidizing solution of the following composition:

| | |
|---|---|
| 200-volume 60% hydrogen peroxide | 8.3 to 25 ml |
| sodium persulphate | 25 to 75 g |
| aqueous ammonia (d = 0.92) | 8.3 to 25 ml |
| Trilon B (ethylenediaminetetra-acetic acid) | 0.5 g |
| water q.s. | 300 ml |

The hair is rinsed copiously and is then washed with a neutralizing shampoo which has the following composition:

| | |
|---|---|
| solution containing 180 g/l of ammonium lauryl sulphate | 25 ml |
| sodium sulphate decahydrate | 1.75 g |
| solution containing 500 g/l of sodium thiosulphate | 1.5 ml |
| tartaric acid | 0.3 g |
| water q.s. | 300 ml |

After washing, the hair is rinsed and then dried.

The quantities of hydrogen peroxide, sodium persulphate and aqueous ammonia vary, depending on the degree (low, medium or high) of bleaching which it is desired to obtain.

"Permanent-waved bleached hair" is the term applied to hair which has first been bleached according to the method described above and then subjected to a permanent-waving treatment by applying for 15 minutes a reducing composition containing 8 g of thioglycolic acid and 2 g of thiolactic acid in 100 g of water and adjusted to pH=8.2 with aqueous ammonia.

After rinsing, a "fixing" solution, consisting of 2.5% hydrogen peroxide, is applied for 15 minutes. The hair is rinsed and then dried.

It is obvious that the composition in accordance with the invention may be applied to any head of hair, provided that it fulfils the conditions defined above, when it is applied to bleached or permanent-waved bleached hair.

The para-phenylenediamines which can be more particularly employed in accordance with the invention are chosen from para-phenylenediamine, para-tolylene-diamine, 2,6-dimethyl-para-phenylenediamine, 2,5-dimethyl-para-phenylenediamine, 2,3-dimethyl-para-phenyl-enediamine, 2-chloro-para-phenylenediamine, 2-methoxy-para-phenylenediamine, 2-α-hydroxymethyl-para-phenylene-diamine, 2-β-hydroxyethyl-para-phenylenediamine, 2-isopropyl-para-phenylenediamine and 2,6-dimethyl-3-methoxy-para-phenylenediamine.

The preferred oxidation dye precursor belonging to the group (A) of single bases is para-phenyl-enediamine. diamine.

The compounds of formula (II) are chosen more particularly from N,N'-bis[(4-amino)phenyl]tetramethylenediamine, N,N'-bis(β-diethylaminoethyl)-N,N,-bis[(4amino)phenyl]tetramethylenediamine, N-(4-hydroxy)phenyl-N'-[(4'-amino)phenyl]ethylenediamine, N,N'-bis(β-hydroxy-ethyl)-N,N'-bis(4-aminophenyl)ethylenediamine, N,N'-bis(β-4'-aminophenyl)-1,3-diamino-2-propanol, N,N'-bis(β-hydroxyethyl)-N,N'-bis(4'-aminophenyl)-1,3-diamino-2-propanol and N,N'-bis(ethyl)-N,N'-bis(4'-amino)-3,methylphenyl)ethylenediamine. These double bases are known, except for N,N'-bis(α-hydroxyethyl)-N,N'-bis(4-aminophenyl)-1,3-diamino-2-propanol and N,N'-bis(ethyl)-N,N'-bis(4-amino-3'-methylphenyl)ethylenediamine, which are new and whose method of preparation is described later.

In accordance with the invention, the dyes of group (A) and of group (B) are present in a total concentration not exceeding 6%, based on the total weight of the composition, this concentration being between 0.01 and 6% and preferably between 0.02 and 3%.

The molar ratio of the single base defined in group (A) to the double base defined in group (B) is preferably between 3 and 10 and in particular between 3.5 and 7.

In addition to the dye precursors belonging to groups (A) and (B) defined above, the compositions in accordance with the invention may also contain one or more tinters or couplers.

Among the couplers there may be mentioned in particular phenols, meta-diphenols, meta-aminophenols, meta-phenylenediamines, meta-acylaminophenols, metaureidophenols, meta-carbalkoxyaminophenols, α-naphthol and couplers containing an active methylene group, such as β-keto compounds and pyrazolones.

2-Isopropyl-5-methylphenol may be mentioned among phenols.

Among meta-diphenols there may be mentioned:
resorcinol,
2-methylresorcinol,
5-methylresorcinol,
2,4-dihydroxyphenoxyethanol,
resorcinol monomethyl ether, and
2,4-dihydroxyanisole.

Among meta-aminophenols there may be mentioned:
meta-aminophenol,
2-methyl-5-aminophenol,
2-methyl-5-N-(β-hydroxyethyl)aminophenol,
2-methyl-5-N-(β-mesylaminoethyl)aminophenol,
2,6-dimethyl-3-aminophenol,
6-hydroxybenzomorpholine,
and their salts.

Among meta-phenylenediamines there may be mentioned:
meta-phenylenediamine,
2,4-diaminophenoxyethanol,
2,4-dimethoxy-1,3-diaminobenzene,
1,3,5-trimethoxy-2,4-diaminobenzene,
2,4-diaminoanisole,
6-aminobenzomorpholine,
[N-2-(β-hydroxyethyl)amino-4-amino]phenoxyethanol,
[N-4-(β-hydroxyethyl)amino-2-amino]phenoxyethanol,
2-amino-N-(4-β-hydroxyethyl) aminoanisole,
4,5-di(β-hydroxyethoxy)-1,3-diaminobenzene,
1-β-hydroxyethoxy-2,4-diaminobenzene,
and their salts.

Among the other couplers which can be employed in the dye compositions of the invention there should be mentioned phenol or aniline derivatives containing a methylenedioxy heterocyclic ring and more particularly:
3,4-methylenedioxyphenol,
3,4-methylenedioxyaniline,
2-bromo-4,5-methylenedioxyphenol,
2-chloro-4,5-methylenedioxyphenol,
2-methoxy-4,5-methylenedioxyaniline,
and pyridine derivatives, such as 2,6-dihydroxypyridine, 2,6-diaminopyridine and 4-methyl-2,6-dihydroxypyridine.

When present, couplers may be incorporated in the compositions in accordance with the invention in free form or in a salt form, in proportions of up to 10% and preferably from 0 to 6% of the weight of the composition.

The compositions in accordance with the invention may also contain para-phenylenediamines other than those of formula (I), containing a primary amine functional group, in particular para-phenylenediamines containing a tertiary or secondary amine group, such as more particularly 1-N, N-dimethylamino-4-aminobenzene, 1-N, N-diethylamino-4-aminobenzene, 1-N, N-(bis-β-hydroxyethyl)-amino- 4-aminobenzene, 1-N-β-methoxyethylamino-4-aminobenzene or 1-N-β-hydroxypropyl-4-aminobenzene.

Other oxidation dye precursors which may be present in the compositions in accordance with the invention may be p-aminophenol and its derivatives, substituted on the benzene nucleus or on the amine functional group, pyridine or pyrimidine derivatives and more particularly 2,5-diaminopyridine and its derivatives which are N-substituted in position 2, 2,4,5,6-tetraaminopyrimidine and its derivatives which are substituted on the nitrogen atom.

The other dye precursors may be present in the compositions in accordance with the invention in proportions which can be up to 5% by weight relative to the total weight of the composition.

The compositions in accordance with the invention may also contain direct dyes belonging more particularly to the groups of nitrobenzene dyes, anthraquinone dyes and azo dyes, this being with a view to contributing highlights to the colour.

The direct dyes are present in the compositions in accordance with the invention in proportions ranging from 0 to 5% and preferably from 0 to 2% by weight relative to the total weight of the composition.

The compositions in accordance with the invention may be presented in various forms: more or less thickened liquids, liquids which can be gelled by dilution, more or less thick creams, and may optionally be packaged as an aerosol.

Very many cosmetically acceptable ingredients may combine in obtaining the desired form and in particular in resulting in the expected cosmetic product when the composition is intended for dyeing living human hair.

Cosmetically acceptable solvents, surface-active agents, thickening agents, perfumes, preservatives, alkalifying or acidifying agents, waxes and fatty substances, hair-treatment agents, sequestering agents and reducing agents may be added to these compositions.

The compositions in accordance with the invention generally comprise an aqueous medium consisting of water or a water-solvent(s) mixture, the solvent(s) being preferably chosen from organic solvents such as ethyl alcohol, propyl or isopropyl alcohol, tert-butyl alcohol, benzyl alcohol, phenylethyl alcohol, ethylene glycol, ethylene glycol monomethyl, monoethyl and monobutyl ethers, polyethylene glycols, ethylene glycol monoethyl ether acetate, propylene glycol, propylene glycol and dipropylene glycol monomethyl ethers, or methyl lactate.

The solvents are present in concentrations of between 0.5 and 75% by weight relative to the total weight of the composition, when the composition consists of a water-solvent(s) mixture.

The surface-active agents are chosen from anionic, cationic, non-ionic and amphoteric surfactants or mixtures thereof, and are present in proportions of between 0.1 and 50% by weight.

The thickening agents may be chosen from sodium alginate, gum arabic, guar gum, biopolymers such as xanthan gum or scleroglucans, cellulose derivatives such as methyl cellulose, hydroxyethyl cellulose and hydroxypropyl methyl cellulose, and the sodium salt of carboxymethyl cellulose and of acrylic acid polymers.

It is also possible to employ inorganic thickening agents such as bentonite.

These thickeners, employed by themselves or mixed, are preferably present in proportions of between 0.1 and 5% by weight relative to the total weight of the composition, and advantageously between 0.5 and 3% by weight.

The acidifying agents which can be employed in accordance with the invention may be chosen from lactic acid, acetic acid, tartaric acid, phosphoric acid, hydrochloric acid and citric acid.

The alkalifying agents are preferably chosen from alkali metal or anunonium hydroxides or carbonates, and amines such as alkanolamines and alkylamines.

When the composition is employed in an aerosol device, it may be packaged under pressure with a view to forming a foam in the presence of a propellant and at least one foam generator. The foam-generating agents may be anionic, cationic, nonionic, amphoteric polymers or surface-active agents of the type of those defined above.

The dye compositions in accordance with the invention are generally employed mixed with an oxidizing agent at the time of use. This oxidizing agent may be hydrogen peroxide, urea peroxide or persalts, such as persulphates or perborates. In the final dye composition which can be applied to hair, this oxidizing agent is present in a proportion ranging from 0.5 to 80% by weight.

The composition in accordance with the invention may be produced beforehand and stored or may be prepared just before use, in which case the composition is applied to hair with an oxidizing agent, using a treatment time which may range from 5 minutes to 1 hour.

After the application and the treatment the hair is rinsed, optionally washed, and then dried.

According to an alternative form of the invention, it is possible to store the dye precursors in separate compositions and either to mix Just before use or to apply these different compositions in two steps. It is possible, in this connection, to apply, in a first step, the composition containing the dye precursors of group A which are chosen from para-phenylenediamines, and then after a treatment time and optional rinsing, in a second step, the second composition containing the double bases.

For both of these compositions the treatment times are between 5 and 45 minutes.

Just as before, after the treatment time the hair is rinsed, optionally washed, rinsed again and dried.

In this latter embodiment, the composition in accordance with the invention may be stored in the form of a kit with two compartments, the first of which compartments contains, in a suitable medium for dyeing, of group A as defined above and the second of which contains composition B comprising the dye precursors of formula (II).

The compositions present in both of these compartments may also contain the other dyes or dye precursors or ingredients defined above.

The examples which follow are intended to illustrate the invention without, however, being limiting in nature.

EXAMPLE OF PREPARATION 1

Preparation of
N,N'-bis($\beta$-hydroxyethyl]-N,N'-bis(4-aminophenyl)-1,3-diamino-2-propanol 1st stage:

Preparation of N,N'-bis($\beta$-hydroxyethyl)-N,N'-bis(-phenyl)-1,3-diamino-2-propanol The mixture consisting of 2 moles (274.4 g) of N-$\beta$-hydroxyethylaniline, 140 g of calcium carbonate and 1.2 moles (154.8 g) of 1,3-dichloro-2-propanol in 1 liter of water is heated for 6 hours under water reflux.

The expected product crystallizes after cooling and neutralization with 50 ml of concentrated hydrochloric acid.

After filtering off and washing with water the product obtained is recrystallized from isopropyl alcohol. 238 g of the expected product are obtained. It melts at 120° C.

Analysis of the product obtained gives the following results:

| Analysis for $C_{19}H_{26}N_2O_3$ | | | | |
|---|---|---|---|---|
| | C % | H % | N % | O % |
| Calculated | 69.06 | 7.93 | 8.48 | 14.53 |
| Found | 69.13 | 7.96 | 8.38 | 14.82 |

2nd stage:

Preparation of N,N'-bis($\beta$-hydroxyethyl)-N,N'-bis(4-nitrosophenyl)-1,3-diamino-2-propanol A solution of 1.14 moles (78.7 g) of sodium nitrite in 150 ml of water is added dropwise at between 0° C. and 5° C. to a solution of 0.5 mole (165.2 g) of N,N'-bis($\beta$-hydroxyethyl)-N,N'-bis(phenyl)-1,3-diamino-2-propanol prepared in the preceding stage, 290 ml of concentrated hydrochloric acid and 900 g of ice. After the end of addition stirring is continued for 1 hour 30 minutes. The reaction medium is neutralized by adding 300 ml of 20% strength aqueous ammonia at 10° C. After filtering off, the product obtained is again made into a paste with water. It can be used wet for the following stage.

3rd stage :

Preparation of N,N'-bis-$\beta$-hydroxyethyl)-N,N'-bis[(4'-amino)phenyl]-1,3-diamino-2-propanol tetrahydrochloride hydrate 0.58 moles (22.6 g) of the dinitroso derivative prepared in the preceding stage are added portion wise to 930 ml of 96° ethyl alcohol containing 135 ml of water, 11.9 g of ammonium chloride and 390 g of finely powdered zinc and heated under reflux. At the end of addition the heating is continued for 1 hour.

The zinc is removed by filtering the reaction mixture hot and the expected product is precipitated by adding to the filtrate 340 ml of a solution of hydrochloric acid in absolute ethanol (7.5 N). 234 g of expected product are obtained, after drying, by adding ethyl ether.

Analysis of the product obtained gives the following results:

| Analysis for $C_{15}H_{26}N_4O_2Cl_4$ | | | | | |
|---|---|---|---|---|---|
| | C % | H % | N % | O % | Cl % |
| Calculated | 43.53 | 6.53 | 10.68 | 12.21 | 27.05 |
| Found | 43.72 | 6.57 | 10.37 | 12.16 | 27.10 |

EXAMPLE OF PREPARATION 2

Preparation of
N,N'-bis(ethyl)-N,N'-bis(4'-amino-3'-methylphenyl)ethylenediamine tetrahydrochloride hydrate 1st stage Preparation of N,N'-bis(ethyl)-N,N'-bis(3,-methylphenyl)ethylenediamine dihydrochloride.

The mixture consisting of 1 mole (135.2 g) of N-ethyl-m-toluidine, 60 g of calcium carbonate and 0.55 mole (104 g) of 1,3-dibromoethane is heated under reflux for 15 hours.

After cooling and neutralization with 60 ml of concentrated hydrochloric acid, followed by extraction with ethyl acetate, the expected product is obtained and is converted into the dihydrochloride with a solution of hydrochloric acid in absolute ethanol.

The product is recrystallized from absolute ethanol.

Analysis of the product obtained gives the following results:

| Analysis for $C_{20}H_{30}N_2Cl_2$ | | | | |
|---|---|---|---|---|
| | C % | H % | N % | Cl % |
| Calculated | 65.04 | 8.18 | 7.58 | 19.20 |
| Found | 65.14 | 8.17 | 7.52 | 19.12 |

2nd Stage
Preparation of N,N'-bis(ethyl) -N,N'-bis(3'-methyl-4'-nitrosophenyl)ethylenediamine.

A solution of 0.106 moles (7.3 g) of sodium nitrite in 17 ml of water is added dropwise at 0° C. to a solution of 0.05 moles (18.5 g) of N,N'-bis(ethyl)-N,N'bis(3'-methylphenyl)ethylenedia/nine, in the dihydrochloride form prepared in the preceding stage, 20 ml of concentrated hydrochloric acid and 105 g of ice. After the end of addition the stirring is continued for 30 minutes. The hydrochloride of the expected product crystallizes.

The expected product precipitates on adding 15 ml of 20% strength aqueous ammonia to a suspension of the product obtained in 200 ml of water. It is recrystallized from 200 ml of 96° C. ethanol and melts at 157° C.

Analysis of the product obtained gives the following results:

| Analysis for $C_{20}H_{26}N_4O_2$ | | | | |
|---|---|---|---|---|
| | C % | H % | N % | O % |
| Calculated | 67.77 | 7.39 | 15.81 | 9.03 |
| Found | 68.03 | 7.42 | 16.06 | 9.16 |

3rd Stage
Preparation of N,N'-bis(ethyl)-N,N'-bis(4'-amino-3'methylphenyl)ethylenediamine tetrahydrochloride hydrate.

0.039 moles (14.1 g) of the dinitroso derivative prepared in the preceding stage are added portion wise to 60 ml of 96° C. ethyl alcohol containing 8 ml of water, 0.8 g of ammonium chloride and 31 g of finely powdered zinc and heated under reflux. After the end of addition heating is continued for 30 minutes.

The zinc is removed by filtering the reaction mixture hot. The expected product is obtained after adding an ethanolic solution of hydrochloric acid and evaporating to dryness.

Analysis of the product obtained after purification in ethanol containing hydrogen chloride gives the following results:

| Analysis for $C_{20}H_{36}N_4OCl_4$ | | | | | |
|---|---|---|---|---|---|
| | C % | H % | N % | O % | Cl % |
| Calculated | 48.99 | 7.40 | 11.43 | 3.26 | 28.92 |
| Found | 48.88 | 7.46 | 11.37 | 3.40 | 28.75 |

EXAMPLES OF FORMULATION

EXAMPLE 1

| | |
|---|---|
| N,N'-Bis($\beta$-hydroxyethyl)-N,N'-bis-[(4-amino)phenyl]ethylenediamine (dihydrochloride) | 0.15 g |
| para-Phenylenediamine | 0.15 g |
| Polyethylene glycol 300 | 10.0 g |
| Ammonium lauryl sulphate | 16.0 g |
| $C_{12}$–$C_{14}$ alcohols oxyethylenated with 12 moles of ethylene oxide | 4.0 g |
| Pentasodium salt of diethylenetriamine-pentaacetic acid | 0.2 g |
| Sodium metabisulphite | 0.4 g |
| Resorcinol | 0.3 g |
| 20% $NH_4OH$ | 10.0 g |
| Water q.s. | 100.0 g |

This is mixed with an equal weight of 20-volume hydrogen peroxide at the time of use.

When applied for 30 minutes to hair sensitized unevenly over its entire length, a dark brown colour is obtained after rinsing, washing and drying.

$V_B-V_{PB}=-0.2$.

EXAMPLE 2

| | |
|---|---|
| N,N'-Bis(4'-aminophenyl)-1,3-diamino-2-propanol tetrahydrochloride | 0.15 g |
| para-Phenylenediamine | 0.15 g |
| Polyethylene glycol 300 | 10.0 g |
| Ammonium lauryl sulphate | 16.0 g |
| $C_{12}$–$C_{14}$ alcohols oxyethylenated with 12 moles of ethylene oxide | 4.0 g |
| Pentasodium salt of diethylenetriamine-pentaacetic acid | 0.2 g |
| Sodium metabisulphite | 0.4 g |
| Resorcinol | 0.3 g |
| 20% $NH_4OH$ | 10.0 g |
| Water q.s | 100.0 g |

An equal weight of 20-volume hydrogen peroxide is added at the time of use.

When applied for 30 minutes to hair sensitized unevenly over its entire length, this composition gives it a dark brown colour after rinsing and washing.

$V_B-V_{PB}=+0.1$.

EXAMPLE 3

| | |
|---|---|
| N,N'-Bis($\beta$-hydroxyethyl)-N,N'-bis-(4'-aminophenyl)-1,3-diamino-2-propanol (tetrahydrochloride) | 0.15 g |
| para-Phenylenediamine | 0.15 g |
| Polyethylene glycol 300 | 10.0 g |
| $NH_4$ lauryl sulphate | 16.0 g |
| $C_{12}$–$C_{14}$ alcohols oxyethylenated with 12 moles of ethylene oxide | 4.0 g |
| Pentasodium salt of diethylenetriamine-pentaacetic acid | 0.2 g |
| Sodium metabisulphite | 0.4 g |
| Resorcinol | 0.3 g |
| 20% $NH_4OH$ | 10.0 g |
| Water q.s. | 100.0 g |

Same method of application as in Examples 1 and 2. Dark brown colour.

$V_B-V_{PB}=0$.

EXAMPLE 4

Similar to Example 3, but para-phenylenediamine is replaced with the same quantity of para-tolylenediamine.

Light brown colour.

$V_B-V_{PB}=+0.4$.

EXAMPLE 5

| | |
|---|---|
| N,N'-Bis(β-hydroxyethyl)-N,N'-bis-(4'-aminophenyl)-1,3-diamino-2-propanol (tetrahydrochloride) | 0.07 g |
| para-Phenylenediamine | 0.07 g |
| Polyethylene glycol 300 | 10.0 g |
| NH$_4$ lauryl sulphate | 16.0 g |
| C$_{12}$–C$_{14}$ alcohols oxyethylenated with 12 moles of ethylene oxide | 4.0 g |
| Pentasodium salt of diethylene-triaminepentaacetic acid | 0.2 g |
| Sodium metabisulphite | 0.4 g |
| Resorcinol | 0.14 g |
| 2-Methylresorcinol | 0.01 g |
| 20% NH$_4$OH | 10.0 g |
| Water q.s. | 100.0 g |

Same method of application as in Examples 1 and 2. Dark blond colour.

$V_B - V_{PB} = +0.1$.

EXAMPLE 6

| | |
|---|---|
| N,N'-Bis(ethyl)-N,N'-bis(4'-amino-3'-methylphenyl)ethylenediamine tetrahydrochloride hydrate | 0.7 g |
| para-Phenylenediamine | 0.7 g |
| Polyethylene glycol 300 | 10.0 g |
| Ammonium lauryl sulphate | 16.0 g |
| C$_{12}$–C$_{14}$ alcohol oxyethylenated with 12 moles of ethylene oxide | 4.0 g |
| Resorcinol | 0.14 g |
| 2-Methylresorcinol | 0.01 g |
| Sodium metabisulphite | 0.04 g |
| Pentasodium salt of diethylene-triaminepentaacetic acid | 0.2 g |
| 20% aqueous ammonia | 10.0 g |
| Water q.s. | 100.0 g |

An equal weight of 20-volume hydrogen peroxide is added at the time of use.

When applied for 30 minutes to hair sensitized unevenly over its whole length, this composition gives it a dark brown colour after rinsing and washing.

$V_B - V_{PB} = +0.3$.

We claim:

1. Dye composition for dyeing keratinous fibres, comprising:
   (a) at least one single base dye precursor selected from the group consisting of para-phenylenediamines of formula (I):

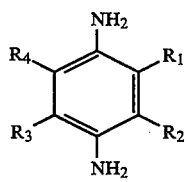

(I)

wherein R$_1$ denotes a halogen atom or a C$_1$–C$_4$ alkyl or C$_1$–C$_4$ alkoxy radical and R$_2$, R$_3$ and R$_4$, independently of one another, denote a hydrogen atom or a halogen atom or a C$_1$–C$_4$ alkyl or C$_1$–C$_4$ alkoxy radical, and salts thereof;

(b) at least one double base dye precursor selected from the group consisting of N,N'-diphenylalkylenediamines of the formula (II):

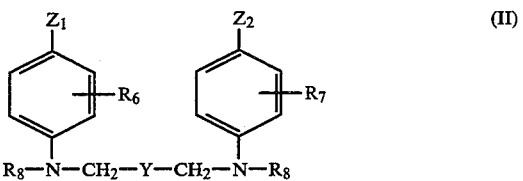

(II)

in which:

Z$_1$ and Z$_2$, which are identical or different, denote hydroxyl or NHR$_9$ groups, in which R$_9$ denotes a hydrogen atom or an alkyl radical;

R$_6$ and R$_7$, which are identical or different, denote hydrogen atoms, halogen atoms or (C$_1$–C$_4$) alkyl groups;

R$_8$ denotes a hydrogen atom, a (C$_1$–C$_4$) alkyl, hydroxy (C$_2$–C$_4$) alkyl, an aminoalkyl group or an aminoalkyl group in which the amino residue is substituted by a (C$_1$–C$_4$) alkyl group; and Y denotes a radical selected from the group consisting of the following radicals:

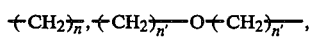

  and

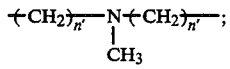

in which:

n is an integer between 0 and 8, and n' is an integer between 0 and 4, and acid addition salts thereof; and (c) a suitable carrier, wherein:

the concentration of said single and double base dye precursors is sufficient for dyeing said keratinous fibres;

said single sand double base dye precursors are selected such that the difference between the value of the intensity of the colour on dyed bleached hair (V$_B$) and the intensity on dyed permanent-waved bleached hair (V$_{PB}$) is 0±0.5, and value is determined using the Munsell system for specifying color; and the molar ratio of the single base dye precursors to the double base dye precursors is between 3.5 and 7.

2. Composition according to claim 1, in which the compounds of formula (I) are chosen from the group consisting of para-tolylenediamine,2,6-dimethyl-para-phenylenediamine,2,5-dimethyl-para-phenylenediamine, 2,3-dimethyl-para-phenylene-diamine, 2-chloro-para-phenylenediamine, 2-methoxy-para-phenylenediamine, 2-α-hydroxymethyl-para-phenylenediamine, 2-β-hydroxyethyl-para-phenylenediamine, 2-isopropyl-para-phenylenediamine and 2,6-dimethyl-3-methoxy-para-phenylenediamine.

3. The composition of claim 1, wherein said double base dye precursor of formula (II) is selected from the group consisting of N,N'-bistetramethylene-diamine, N,N'-bis(β-diethylaminoethyl)-N,N'-bistetramethylenediamine, N-(4-hydroxy)phenyl-N'-ethylenediamine, N,N'-bis(62-hydroxyethyl)-N,N'-bis(4-aminophenyl)ethylenediamine, N,N'-bis(4'-aminophenyl)-1,3-diamino-2-propanol, N,N'-bis(β-hydroxyethyl)-N,N'-bis(4'-aminophenyl),1,3-diamino-2-propanol and N,N'-bis(ethyl)-N,N'-bis(4'-amino-3'-methylphenyl)ethylenediamine.

4. The composition of claim 1, wherein the total concentration of said single and double base dye precursors does not exceed 6% by weight relative to the total weight of the composition.

5. The composition of claim 1 further comprising an effective amount of at least one coupler selected from the group consisting of 2-isopropyl-5-methylphenols, metadiphenols, meta-aminophenols, meta-phenylenediamines, meta-acylaminophenols, meta-ureidophenols, meta-carbalkoxyaminophenols, α-napthol, couplers containing an active methylene group, pyridine derivatives that include a methylenedioxy ring, phenol derivatives that include a methylenedioxy ring and aniline derivatives that include a methylenedioxy ring.

6. The composition of claim 5, wherein the concentration of said coupler is up to 10% by weight relative to the total weight of the composition.

7. The composition of claim 1, further comprising an effective amount of at least one additional dye precursor selected from the group consisting of para-phenylenediamines that include a tertiary or secondary amine group, p-aminophenol, derivatives of p-aminophenol substituted on the benzene nucleus or on the amine functional group, oxidation dye precursors that are amino substituted pyridine or pyrimidine derivatives, and mixtures thereof.

8. The composition of claim 1, further comprising an effective amount of at least one direct dye selected from the group consisting of nitrobenzene dyes, anthraquinone dyes and azo dyes, wherein the concentration of said direct dyes is of up to 5% by weight relative to the total weight of the composition.

9. The composition of claim 1, which is a liquid a cream, or is packaged in aerosol form.

10. The composition of claim 1, wherein said carrier is water or a mixture of water and at least one solvent at a concentration of between 0.5 and 75% by weight relative to the total weight of the composition.

11. The composition of claim 1, further comprising surface-active agents at a concentration of between 0.1 and 50% by weight.

12. The composition of claim 1, further comprising thickening agents at a concentration of between 0.1 and 5% by weight relative to the total weight of the composition.

13. The composition of claim 1, further comprising an effective amount of at least one adjuvant selected from perfumes, preservatives, alkalifying agents, acidifying agents, waxes, fatty substances, hair-treatment agents, sequestering agents and reducing agents.

14. The composition of claim 1, further comprising a foam generator and a propellant, wherein said composition is packaged under pressure, whereby said composition is dispensed as a foam.

15. The composition of claim 4, wherein the total concentration of said single and double base dye precursors relative to the total weight of the composition is between 0.01 and 6%.

16. The composition of claim 6, wherein the concentration of said coupler is up to 6% by weight relative to the total weight of the composition.

17. The composition of claim 1, further comprising at least one oxidizing agent at a concentration of 0.5 to 80% by weight relative to the total weight of the composition, wherein said agent is effective for converting said precursors to dyestuff.

18. A process for dyeing keratinous fibers, comprising applying an oxidizing agent and components (a) and (b) to said fibers, wherein:

component (a) contains a suitable medium for dyeing keratinous fibers and at least one single base dye precursor selected from the group consisting of para-phenylenediamines of formula (I):

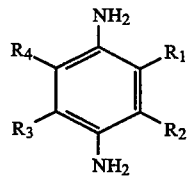

(I)

wherein $R_1$ denotes a halogen atom or a $C_1$-$C_4$ alkyl or $C_1$-$C_4$ alkoxy radical and $R_2$, $R_3$ and $R_4$, independently of one another, denote a hydrogen atom or a halogen atom or a $C_1$-$C_4$ alkyl or $C_1$-$C_4$ alkoxy radical, and salts thereof; and component (b) contains a suitable medium for dyeing keratinous fibers and at least one double base dye precursor selected from the group consisting of N,N'-diphenylalkylenediamines of the formula (II):

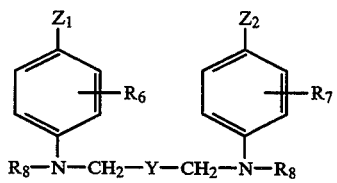

(II)

and acid addition salts thereof;

said components (a) and (b) are applied to said fibers either separately or are mixed immediately prior to use;

said dye precursors are at concentrations in said components that are sufficient for dyeing said keratinous fibers, are selected such that the difference between the value of the intensity of the color on dyed bleached hair ($V_B$) and the value of the intensity on dyed permanent-waved bleached hair ($V_{PB}$) is $0 \pm 0.5$ and said values are determined using the Munsell Systems for specifying color;

the molar ratio of the single base dye precursors to double base dye precursors is between 3 and 10;

$Z_1$ and $Z_2$, which are identical or different, denote hydroxyl or $NHR_9$ groups, in which $R_9$ denotes a hydrogen atom or an alkyl radical;

$R_6$ and $R_7$, which are identical or different, denote hydrogen atoms, halogen atoms or ($C_1$-$C_4$) alkyl groups;

$R_8$ denotes a hydrogen atom, a ($C_1$-$C_4$) alkyl, hydroxy ($C_2$-$C_4$) alkyl, an aminoalkyl group or an aminoalkyl group in which the amino residue is substituted by a ($C_1$-$C_4$) alkyl group; and Y denotes a radical selected from the group consisting of the following radicals:

$-(CH_2)_{\overline{n}}-, -(CH_2)_{\overline{n'}}-O-(CH_2)_{\overline{n'}}-,$ $-(CH_2)_{\overline{n'}}-CHOH-(CH_2)_{\overline{n'}}-$ and $-(CH_2)_{\overline{n'}}-\underset{\underset{CH_3}{|}}{N}-(CH_2)_{\overline{n'}}-;$ in which:

n is an integer between 0 and 8, and n' is an integer between 0 and 4; and wherein said oxidizing agent is present in an amount effective to convert said precursors to dyestuff.

19. The process of claim 18, wherein said components (a) and (b) are applied to the keratinous fibers in separate steps.

20. The process of claim 18, wherein said components (a) and (b) are mixed before application to said keratinous fibers.

21. The process of claim 20, wherein said components (a) and (b) are mixed immediately before use.

22. The process of claim 18, wherein said fibers are human hair.

23. The process of claim 19, wherein said components (a) and (b) are stored in separate compartments of a multicompartment kit prior to being applied to the keratinous fibers in separate steps.

24. The process of claim 21, wherein said components (a) and (b) are stored in separate compartments of a multicompartment kit prior to being mixed immediately before use.

* * * * *